US00PP27364P3

(12) United States Plant Patent
Austin

(10) Patent No.: US PP27,364 P3
(45) Date of Patent: Nov. 15, 2016

(54) ***ROSA HYBRIDA* SHRUB NAMED 'AUSWHIRL'**

(50) Latin Name: *Rosa hybrida*
Varietal Denomination: AUSwhirl

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 9 days.

(21) Appl. No.: 14/545,306

(22) Filed: Apr. 20, 2015

(65) Prior Publication Data

US 2016/0057902 P1 Feb. 25, 2016

(51) Int. Cl.
*A01H 5/02* (2006.01)

(52) U.S. Cl.
USPC ..... Plt./104

(58) Field of Classification Search
USPC ..... Plt./104
CPC ..... A01H 5/0222
See application file for complete search history.

*Primary Examiner* — Kent L Bell
(74) *Attorney, Agent, or Firm* — KPPB LLP

(57) ABSTRACT

A variety of rose plant of the shrub class, named 'AUSwhirl'. The 'AUSwhirl' is a variety of a rose having a yellow bloom with a strong, unfading color, the petals of which are informal with a neat outer ring, and that has a strong fragrance that smells distinctly of lemon, and that also has a growth that is low and rounded with shiny foliage.

1 Drawing Sheet

Classification: The present invention relates to a new *Rosa hybrida* shrub of the market class 'English Rose'.

Variety denomination: The new plant has the varietal denomination 'AUSwhirl'.

CROSS-REFERENCE TO RELATED APPLICATION

The present application claims priority to European CPVO 2014/2054, filed Aug. 21, 2014.

ORIGIN OF INVENTION

This invention relates to a new and distinct variety of shrub rose plant named 'AUSwhirl', which was originated from the cross-pollination of the two 'unnamed' and unpatented seedlings of *Rosa hybrida.*

BACKGROUND OF THE INVENTION

The primary objective of this breeding was to produce a rose variety having a yellow bloom with a strong, unfading color, the petals of which are informal with a neat outer ring, and that has a strong fragrance that smells distinctly of lemon, and that also has a growth that is low and rounded with shiny foliage.

SUMMARY OF THE INVENTION

Among the features which distinguish the new variety from others presently available and commercial rose cultivars known to the inventor is the following combination of characteristics: blooms having an unfading, strong yellow color with an informal arrangement of petals within a neat outer ring of petals, and low rounded growth that has shiny foliage, and a strong lemon fragrance.

Asexual reproduction of the new variety by budding as performed at Bowling Green Lane in Albrighton, Britain shows that the foregoing and other distinguishing characteristics come true to form and are established and transmitted through succeeding asexual propagations. 'AUSwhirl' may be asexually propagated by budding. The budding successfully occurred on the plant/rootstock *Rosa dumetorum* 'Laxa' for the observed plants.

COMPARISON WITH PARENTS

The seed and pollen parents of 'AUSwhirl' are two unnamed seedlings. The new rose may be distinguished from its seed parent, by the following combination of characteristics: the seed parent is more disease prone with larger pink flowers. The new rose may be distinguished from its pollen parent, by the following combination of characteristics: the parent is a deeper shade of yellow, with larger flowers and is more disease-prone.

COMPARISON WITH THE CLOSEST COMMERCIALLY AVAILABLE CULTIVAR

The closest commercially available cultivar to the new variety is the 'AUSmol' (U.S. Plant Pat. No. 9,524) and 'AUSbaker' (unpatented). The new rose may be distinguished from the 'AUSmol' and 'AUSbaker' varieties by the following combination of characteristics: the 'AUSmol' (110-120) and 'AUSbaker' (110) roses have more petals than 'AUSwhirl' (77). The arrangement of petals also differs, in 'AUSwhirl' the petal arrangement is informal whereas for 'AUSmol' it is a regular rosette formation and for 'AUSbaker' the blooms are quartered. Finally, 'AUSwhirl' forms a low, rounded shrub whereas 'AUSmol' is upright and short, and 'AUSbaker' is tall and will grow as a climber.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUSwhirl' specimens were made in Albrighton, Wolverhampton, United Kingdom. The following description is of 1 year-old potted rose plants of the new variety grown in a garden environment in Albrighton, Britain in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

- *Size*.—About 2.2 cm long and 1.8 cm in diameter when the petals start to unfurl.
- *Form*.—The bud form is pointed ovoid.
- *Color*.—When sepals first divide, the bud color is RHS 151B (yellow-green group) with RHS 45A (red group). When half blown, the upper sides of the petals are RHS 12A (yellow group), and the lower sides of the petals are RHS 12B (yellow group).
- *Calyx*.—Shape: star-shaped when the bloom is open and folds back against the stem. Length: 2.6 cm. Diameter: 1.3 cm.
- *Sepals*.—Arrangement: Regularly arranged. Color: Upper Surface: green RHS 147C (yellow-green group). Lower Surface: green RHS 146C (yellow-green group) with RHS 47A (red group). Length: 2.6 cm. Width: 1 cm. Shape: Lanceolate. Surface texture: Upper Surface: Downy. Lower Surface: Smooth. Number: There are 3 lightly appendaged sepals, and 2 unappendaged sepals with downy edges.
- *Receptacles*.—Color: RHS 144A (yellow-green group). Shape: funnel. Size: medium, about 1.2 cm high×1 cm wide. Surface: Smooth.
- *Peduncle*.—Length: medium, averaging about 10 cm. Surface: Glandular. Color: RHS 144A (yellow-green group) with RHS 47A (red group). Strength: Strong.

Blooms:

- *Size*.—Large, average open diameter is about 10 cm.
- *Borne*.—Several together in clusters of 3-4 with blooms having a rounded shape.
- *Stems*.—Strength: Normal, average length is about 30-40 cm. Diameter: 3-4 mm.
- *Form*.—When first open, bloom is cupped. Permanence of bloom: outer petals curl back.

Petalage: Number of petals under normal conditions: 77.

- *Color*.—The upper sides of the petals are RHS 12A (yellow group). The reverse sides of the petals are RHS 12A (yellow group).
- *Variegations*.—None.
- *Discoloration*.—The general tonality at the end of the first day is RHS 12A (yellow group), and at the end of the third day is RHS 12A (yellow group).
- *Fragrance*.—Strong. Character of fragrance: fruity (lemon).

Petals:

- *Texture*.—Smooth.
- *Size*.—Width: 3.3 cm. Length: 4.5 cm.
- *Surface*.—Smooth.
- *Shape*.—Obovate.
- *Margin*.—Variable, some petals with entire margins and some with incisions.
- *Apex shape*.—Rounded.
- *Base shape*.—Cuspidate.
- *Form*.—Edges slightly quilled.
- *Arrangement*.—Informal.
- *Petaloids*.—Number: 10. Color: RHS 12A (yellow group) Length: 1.9 cm. Width: 6 mm. Shape: Obovate, with some folded. Margin: Irregular.
- *Persistence*.—Petals drop off cleanly before drying.
- *Lastingness*.—On the plant: fair about 5 days. As a cut flower: not tested.

Reproductive parts:

- *Stamens*.—Number: around 30. Length: 6 mm.
- *Anthers*.—Length: 3 mm. Color: RHS 17B (yellow-orange group). Arrangement: Mixed with petaloids.
- *Filaments*.—Color: RHS 20A (yellow-orange group). Length: 8.5 mm.
- *Pollen*.—Color: RHS 17A (yellow-orange group).
- *Pistils*.—Number: 18. Length: 9 mm.
- *Styles*.—Color: RHS 155A (white group). Length: 8 mm.
- *Stigmas*.—Color: RHS 20A (yellow-orange group). Length: 1 mm.
- *Hips*.—None Observed.

PLANT CHARACTERISTICS

Plant form: Shrub.

Plant growth: Medium.

Age to maturity: 2 years.

Mature plant: Height: 120 cm. Width: 90 cm.

Rootstock: Dr. Huey in the U.S. and *Rosa dumetorum* 'Laxa' for the observed plants in the UK.

Foliage:

- *Number*.—Leaflets on normal mid-stem leaves is: 5 (including terminal leaflet), but can vary between 3 and 7.
- *Size*.—There are two sizes: Medium, about 16 cm long×9 cm wide; and Small, about 10 cm long×5.5 cm wide.
- *Quantity*.—Abundant. Number of leaves per flowering stem is: 10.
- *Color*.—New foliage: Upper side: RHS N144A (yellow-green group) tinged with RHS 183A (greyed-purple group). Lower side: RHS 144A (yellow-green group) with RHS 183A (greyed-purple group). Old foliage: Upper side: RHS 137A (green group). Lower side: RHS 138A (green group).

Leaflets:

- *Size*.—Two sizes: About 5.2 cm long×4 cm wide. About 3.5 cm long×2.4 cm wide.
- *Shape*.—Pointed oval.
- *Base shape*.—Rounded.
- *Apex shape*.—Acuminate.

*Texture*.—Leathery.

*Edge*.—Serrated.

*Serrations*.—Double.

*Petiole*.—Color: RHS 144A (yellow-green group). Length: 4 cm. Width: 2 mm. Surface Texture: Glandular.

*Petiole rachis*.—Color: RHS 144A (yellow-green group). Underside: with prickles.

*Stipules*.—Length: 2 cm, glandular. Color: RHS 144A (yellow-green group).

*Auricle*.—Shape: Lanceolate. Length: 2 cm. Width: 3 mm. Color: RHS 144A (yellow-green group).

*Vein color*.—Color: same as leaf color.

*Venation pattern*.—Reticulate.

Wood:

*New wood*.—Color: RHS 183B (greyed-purple group). Bark: Smooth.

*Old wood*.—Color: RHS 144A (yellow-green group) with some RHS 183B (greyed-purple group) showing. Bark: Smooth.

Branching habit:

*Number*.—5.

*Branching dimension*.—Length: 70 cm. Diameter: 6 mm.

Stems:

*Mature stem*.—Length: 90 cm. Diameter: 1 cm.

*Internode distance*.—2-5 cm. The above measurements are all variable, depending on growing conditions in a season.

*Stem pubescence present*.—No.

Prickles:

*Quantity*.—On main canes from base: Many. Number per stem length: 10 per 10 cm. On laterals from main canes: Many. Number per stem length: 10 per 10 cm.

*Form*.—Deep concave.

*Length*.—6 mm.

*Color when young*.—RHS 183A (greyed-purple group).

*Color when mature*.—RHS 199B (red-brown group).

Small prickles:

*Quantity*.—Main stalk: None Laterals: None

Disease resistance:

*Mildew*.—Resistant.

*Blackspot*.—Resistant.

*Rust*.—Resistant.

Pest resistance: Not tested.

Winter hardiness: Not tested.

Growing conditions: Normal garden conditions.

What is claimed is:

1. A new and distinct variety of rose plant of the shrub class, substantially as herein shown and described.

* * * * *

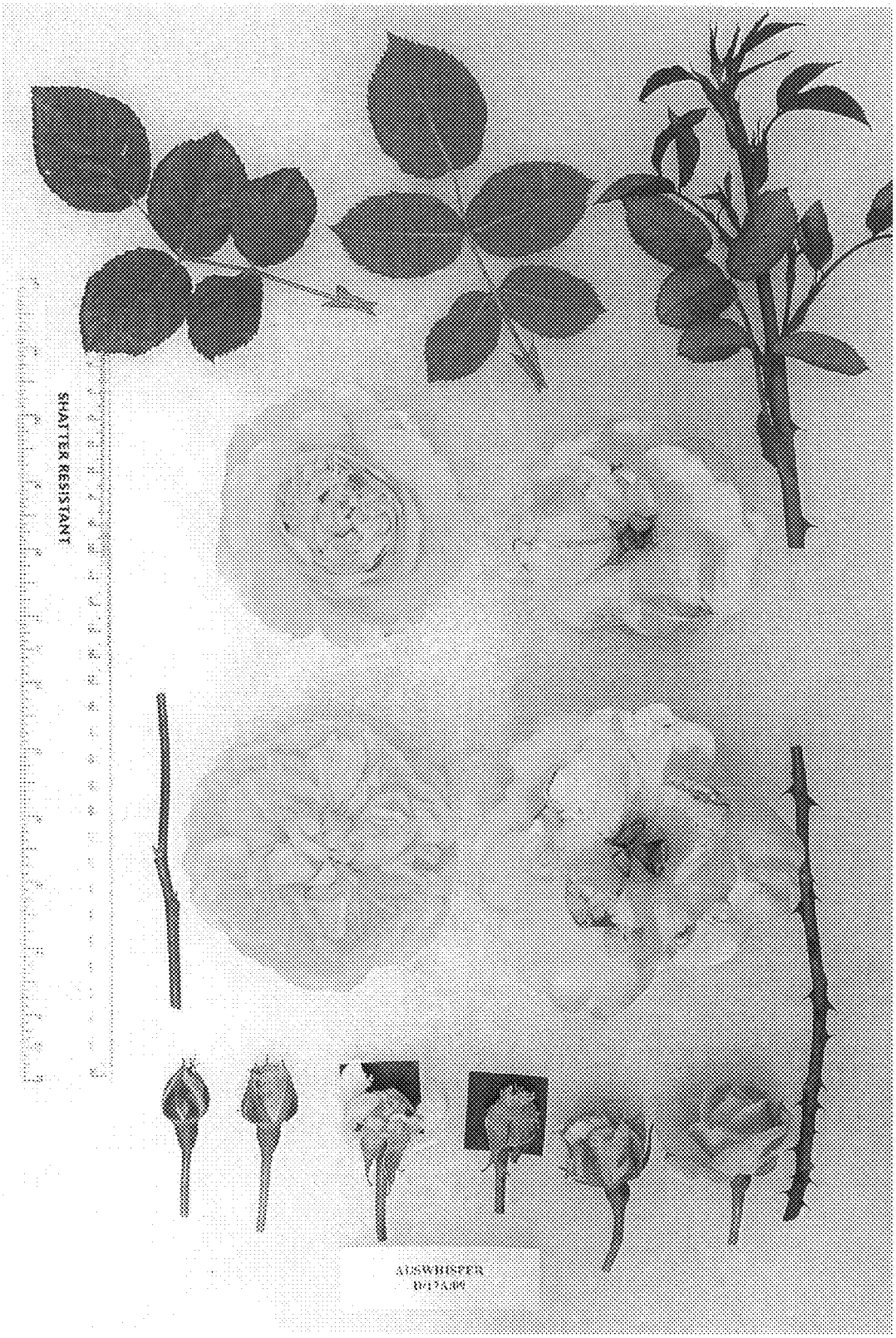
SHATTER RESISTANT
AUSWHISPER
B417A39

UNITED STATES PATENT AND TRADEMARK OFFICE

CERTIFICATE OF CORRECTION

PATENT NO. : PP27,364 P3
APPLICATION NO. : 14/545306
DATED : November 15, 2016
INVENTOR(S) : David J. C. Austin It is certified that error appears in the above-identified patent and that said Letters Patent is hereby corrected as shown below:

In (71), please update Applicant information to "Albrighton, (GB)"
In (72), please update Inventor information to "Albrighton, (GB)"

Signed and Sealed this
Thirtieth Day of May, 2017

Michelle K. Lee

Michelle K. Lee
*Director of the United States Patent and Trademark Office*